United States Patent [19]

Rall

[11] Patent Number: 5,024,532
[45] Date of Patent: Jun. 18, 1991

[54] DEW POINT MEASURING APPARATUS INSTALLATION SYSTEM

[75] Inventor: Dieter Rall, Newport Beach, Calif.
[73] Assignee: Luxtron Corporation, Mountain View, Calif.
[21] Appl. No.: 354,739
[22] Filed: May 22, 1989
[51] Int. Cl.$^5$ .......................................... G01N 25/68
[52] U.S. Cl. ........................................ 374/28; 374/16
[58] Field of Search ..................... 374/28, 27, 25, 16; 73/336.5

[56] References Cited

U.S. PATENT DOCUMENTS

| | | | |
|---|---|---|---|
| 3,134,259 | 5/1964 | Hallmarken | 374/28 |
| 3,173,610 | 3/1965 | Feibush et al. | 374/28 |
| 3,250,114 | 5/1966 | Booth | 374/28 |
| 3,491,583 | 1/1970 | Roussel et al. | 374/28 |
| 3,976,450 | 8/1976 | Marcote et al. | 73/1 G |
| 4,506,994 | 3/1985 | Schwab | 374/28 |
| 4,572,427 | 2/1986 | Selfridge et al. | 219/407 |
| 4,579,462 | 4/1986 | Rall et al. | 374/28 |
| 4,701,415 | 10/1987 | Dutton et al. | 435/289 |

FOREIGN PATENT DOCUMENTS 283352  9/1988  European Pat. Off. ............ 374/28

OTHER PUBLICATIONS

Giedt, "Velocity Distribution in the Entrance Region of a Tube", Chap. 7, Section 10, pp. 149–150, in *Principles of Engineering Heat Transfer*, D. Van Nostrand Company, Inc., 1957.
TransMet Engineering, Inc., "Dew Point Sensor, brochure on Dew Point 9000", 1987.
TransMet Engineering, Inc., "Precise Moisture Control-High Temperature Dew Point Measurement", brochure on Dew Point 9000, 1987.

Primary Examiner—William A. Cuchlinski, Jr.
Assistant Examiner—Diego F. F. Gutierrez
Attorney, Agent, or Firm—Majestic, Parsons, Siebert & Hsue

[57] ABSTRACT

A dew point temperature measuring apparatus is positioned in a sample flow channel that withdraws a sample of a gaseous atmosphere within an enclosure for measuring the dew point temperature of the gaseous atmosphere from which its humidity may be determined. The dimensions of the sample flow channel and the velocity of the gas flow past the dew point temperature measuring apparatus is controlled to assure that the flow is laminar in order to avoid unwanted heat transfer between the sample gas and the dew point temperature measuring apparatus. The dew point temperature measuring apparatus includes a pair of sensors positioned side-by-side in a top wall of the sample flow channel.

5 Claims, 1 Drawing Sheet

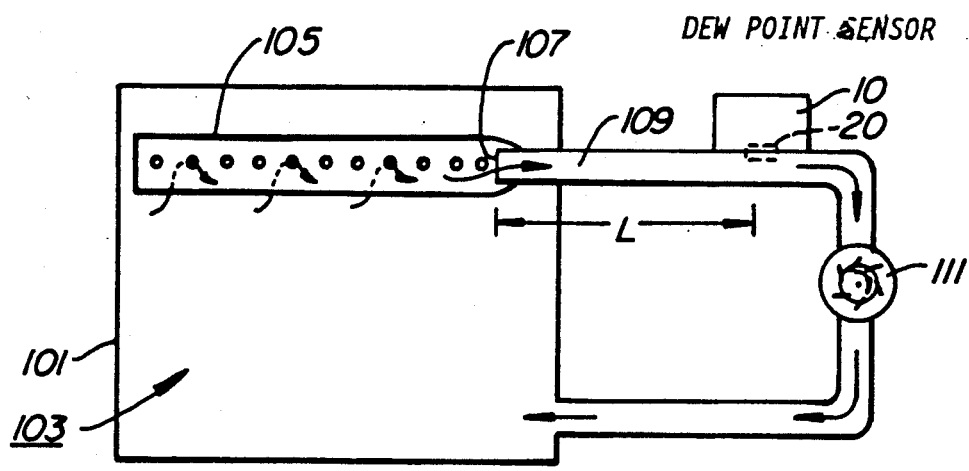
FIG._1.
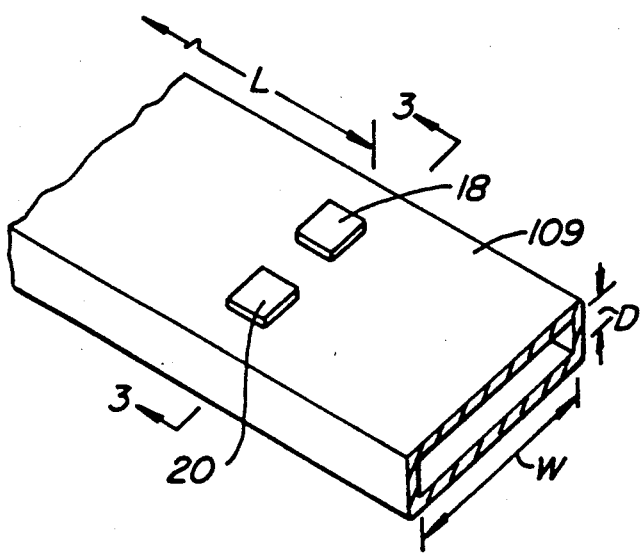
FIG._2.
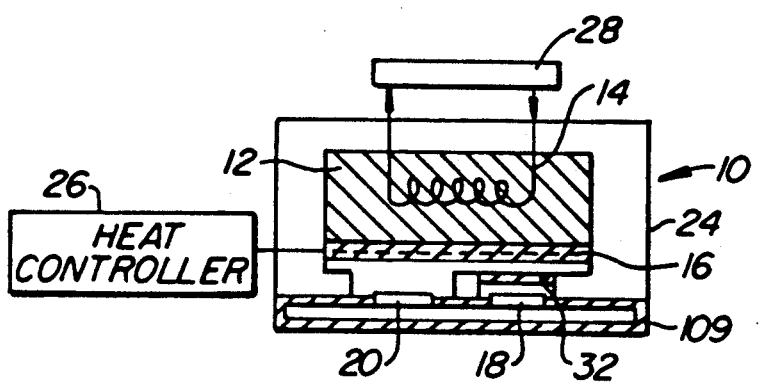
FIG._3.

DEW POINT MEASURING APPARATUS INSTALLATION SYSTEM

BACKGROUND OF THE INVENTION

This invention relates generally to apparatus for measuring the dew point temperature of a gaseous atmosphere in order to establish its relative humidity, and, more specifically, to a technique and system for installing such measuring apparatus in order to improve the accuracy of the measurements made thereby.

U.S. Pat. No. 4,579,462 - Rall et al. (1986) describes a dew point measuring apparatus that utilizes two heat flow sensors in thermal communication with a sample of the gaseous atmosphere whose dew point temperature and/or relative humidity are being measured. One of the heat flow sensors is cycled in temperature to alternate above and below the dew point temperature of the gaseous atmosphere, while the second heat flow sensor is similarly cycled but at a slightly higher temperature in order to avoid reaching the dew point temperature of the gaseous atmosphere.

It is a primary object of the present invention to provide a technique and system for installing such a dew point measuring apparatus in an industrial environment in order to improve the accuracy of the measurement.

SUMMARY OF THE INVENTION

This and additional objects are accomplished by the present invention, wherein, briefly, such a dew point measuring apparatus is mounted with its heat flow sensors positioned in a sample flow channel provided with a fan to remove a continuous sample of the gaseous atmosphere to be measured from an enclosure containing it, the size of the channel and the rate of flow of gas in it being controlled in order to maintain a laminar flow of gas past the sensors. The laminar flow, as opposed to a turbulent flow, results in minimizing the amount of heat which is transferred between each of the sensors and the sampled gas, thereby assuring against obtaining erroneous dew point temperature measurements. The signal-to-noise ratio of the measurement is also improved.

Additional objects, features and advantages of the present invention will become apparent from the following description of a preferred embodiment thereof, which description should be taken in conjunction with the accompanying drawings.

BRIEF DESCRIPTION OF THE DRAWINGS

FIG. 1 schematically illustrates an example of a dew point measuring apparatus installation that utilizes the present invention;

FIG. 2 is a sectional view of a sample flow channel of the measuring system installation according to FIG. 1; and FIG. 3 is a cross-sectional view of a two heat flow sensor type of dew point temperature measuring apparatus, taken at section 3—3 of FIG. 2.

DESCRIPTION OF A PREFERRED EMBODIMENT

In the example system of FIG. 1, an enclosure 101 contains a gaseous atmosphere in a compartment 103 whose dew point temperature and/or relative humidity is to be measured. The enclosure 101 can be an industrial processing chamber, for example, wherein monitoring of the relative humidity is important in order to be able to control processes being performed therein. As another example, the container 101 can be a duct that is carrying gas from one position to another in an industrial process.

In the case of a duct where the gaseous atmosphere of interest is continuously flowing therethrough, it is preferable to extract a sample of the gas along a line across the flow. This is accomplished in the system of FIG. 1 by a perforated tube 105 positioned across the inside of the enclosure 101 at a uniform elevation. Gas is then drawn in through the perforations along the length of the tube positioned across the enclosure.

The perforated tube 105 is connected within the enclosure 101 to an end 107 of a substantially rectangularly shaped sample flow channel 109. A fan 111 is provided in the gas flow path within the channel 109 in order to draw gas out of the enclosure 101 through the perforated tube 105. The fan drives the sample gas past a dew point temperature measuring apparatus 10 and then, as shown in FIG. 1, returns the sample to the compartment 103 within the enclosure 101. Alternatively, the sample can be exhausted to the atmosphere after measurement, depending upon the particular process involved.

Although the invention is described with respect to an example of withdrawing gas from an enclosure in an industrial application, it also can be used to measure the ambient dew point temperature and/or humidity of a room or some other non-industrial environment. In such a case, the end 107 of the sample flow channel 109 is positioned within the room or other environment.

The dew point temperature measuring apparatus 10 of FIG. 1 is described in detail in aforementioned U.S. Pat. No. 4,579,462, the disclosure of which is expressly incorporated herein by reference. Certain portions of that measuring apparatus are shown in the drawings and described herein for completeness of explanation. In that case, the reference characters utilized herein are the same as those used in this prior patent disclosure.

With reference to FIG. 2, a portion of the sample flow channel 109 at the position of the measuring apparatus 10 is illustrated, but the measuring apparatus itself is omitted from that view, for simplicity, except to show the two heat flow sensors 18 and 20 that are positioned across the width of the channel through a top wall thereof. By positioning the sensors in the top wall, accumulation of moisture by condensation, which can occur if the sensors are positioned at the bottom of the channel, is avoided.

In order to maintain laminar flow of the sample gas within the channel 109 as it passes the measuring apparatus 10, the dimensions of the channel, positioning of the measuring apparatus 10 and the rate of flow of gas through the channel provided by the fan 111 are maintained within certain quantitative ranges. The quantitative Reynolds Number ($N_{RE}$) of the flow through the sample channel 119, as calculated from such quantities, needs to be below about 2300, the approximate transition point between laminar and turbulent flow. The desired characteristic of the flow at the heat flow sensor in terms of the Reynolds Number is related to a ratio of the length "L" to a dimension "D" of the interior opening of the sample flow channel 109, by the equation $L/D = 0.05\, N_{RE}$. As shown in FIGS. 1 and 2, the length "L" is the distance from the end 107 of the sample flow channel 109 to the position of the heat flow sensors 18 and 20. The internal dimension "D", as illustrated in FIG. 2, is the narrowest dimension across the internal opening of the channel 109.

It is desired to have a flow with the characteristics below the turbulent/laminar transition point, where the Reynolds number is about 2300. The ratio L/D is thus made to be less than approximately 115, according to the above equation. However, in order to assure laminar flow of the gas past the heat flow sensors 18 and 20, the parameters are preferably set so that the Reynolds Number is about 1000. This results in a ratio L/D of about 50. An example of specific dimensions is for "D" to be about 0.25 inch and "L" to be about 12 inches. The width "W" of the interior of the sample flow channel 109 is set by the volumetric capacity of the fan 111 so that the desired Reynolds Number is obtained at the sensors 18 and 20. The width "W" also needs to be sufficient for mounting the heat flow sensors 18 and 20 side-by-side, and is about 2 inches in the specific example being given.

Therefore, an L/D ratio of less than about 115 provides for laminar flow, but making that ratio significantly less than 115 is generally conservatively chosen to assure continuous laminar flow. The ratio must be high enough, however, in order to allow a sufficient gas sample rate to allow the heat flow sensors to follow changes in the dew point temperature and/or relative humidity of the gaseous atmosphere within the container 101 without too much of a delay.

Referring to FIG. 3, the essential elements of the dew point temperature measuring instrument of aforementioned U.S. Pat. No. 4,579,462 is illustrated. A highly heat conductive block 12, within an external housing 24, includes cooling coils 14 and an electrical resistive heating element 16 embedded therein. The cooling coils 14 are controlled by apparatus 28 to controllably reduce the temperature of the heat sink 12. A heat controller 26 drives the heater 16 in order to controllably raise the temperature of the heat sink 12. This temperature control allows cycling the temperature of the heat flow sensor 20 around the dew point of the gaseous atmosphere being monitored. A layer 32 provides a thermal barrier between the heat sink 12 and the second heat flow sensor 18, resulting in the heat flow sensor 18 operating at a slightly higher temperature than the sensor 20 but also experiencing the same cycles. Signals from the heat flow sensors 18 and 20 are compared in order to determine exactly when condensation occurs on the lower surface of the sensor 20.

Although the present invention has been described with respect to a preferred embodiment, it will be understood that the invention is entitled to protection within the full scope of the appended claims.

What is claimed is:

1. A system for measuring the dew point temperature of a gaseous atmosphere moving within a duct, comprising:

a sample flow channel of given inside dimensions having an open end terminating within said duct and extending outside thereof, said channel being substantially rectangular in cross-section with a height of "D" and a width that is much greater than D, dew point temperature measuring apparatus including a pair of sensors positioned side-by-side in a top wall of said sample channel at a given distance "L" from said channel opened end, means provided as part of said sample flow channel at a position therealong greater than L from said channel opened end for moving a sample of the gaseous atmosphere from within the duct and through said sample channel past said dew point measuring apparatus with a uniform velocity, means connected to said sample flow channel within said duct for causing gases passing thereby to be withdrawn therefrom substantially in a line across said duct, and said given inside dimensions of the sample flow channel and said uniform gas velocity being such that the gas flow past said pair of sensors is characterized by a Reynolds number of substantially 1000, whereby said flow past said pair of sensors is assured to be substantially laminar.

2. The system according to claim 1 wherein said gas withdrawal means includes a perforated tube.

3. The system according to claim 1 wherein said sample flow channel has an opposite end reconnected with said enclosure in a manner to exhaust said gaseous atmosphere back into said enclosure after passing by said dew point temperature measuring apparatus and through said sample moving means.

4. The system according to claim 1 wherein a ratio L/D of said given sample flow channel inside dimensions is equal to or less than substantially 50, the height D being substantially uniform over the distance L.

5. The system according to claim 4 wherein the height D is substantially 0.25 inch.

* * * * *